(12) United States Patent
Bond

(10) Patent No.: US 11,153,328 B2
(45) Date of Patent: *Oct. 19, 2021

(54) SHARING DYNAMICALLY CHANGING UNITS OF CLOUD-BASED CONTENT

(71) Applicant: Box, Inc., Redwood City, CA (US)

(72) Inventor: Michael David Charles Bond, Mountain View, CA (US)

(73) Assignee: Box, Inc., Redwood City, CA (US)

( * ) Notice: Subject to any disclaimer, the term of this patent is extended or adjusted under 35 U.S.C. 154(b) by 155 days.

This patent is subject to a terminal disclaimer.

(21) Appl. No.: 16/684,365

(22) Filed: Nov. 14, 2019

(65) Prior Publication Data
US 2020/0193054 A1 Jun. 18, 2020

Related U.S. Application Data

(63) Continuation of application No. 15/455,074, filed on Mar. 9, 2017, now Pat. No. 10,498,741.
(Continued)

(51) Int. Cl.
*H04L 29/06* (2006.01)
*G06F 21/62* (2013.01)
(Continued)

(52) U.S. Cl.
CPC .......... *H04L 63/105* (2013.01); *G06F 21/602* (2013.01); *G06F 21/604* (2013.01);
(Continued)

(58) Field of Classification Search
CPC .. G06F 21/6218; G06F 21/602; G06F 21/604; G06F 21/6245; H04L 63/0807; H04L 63/0428; H04L 63/105
See application file for complete search history.

(56) References Cited

U.S. PATENT DOCUMENTS 6,314,425 B1  11/2001  Serbinis
7,627,652 B1  12/2009  Commons
(Continued)

OTHER PUBLICATIONS

S. Seo, M. Nabeel, X. Ding and E. Bertino, "An Efficient Certificateless Encryption for Secure Data Sharing in Public Clouds," in IEEE Transactions on Knowledge and Data Engineering, vol. 26, No. 9, pp. 2107-2119, Sep. 2014. (Year: 2014).*
(Continued)

*Primary Examiner* — Kari L Schmidt
(74) *Attorney, Agent, or Firm* — Vista IP Law Group, LLP

(57) ABSTRACT

Systems for managing multiple shared content objects using access tokens that cover the multiple shared content objects are disclosed. A method commences upon assigning the shared content objects to have individual permissions grantable to two or more users. A user configures a shareable unit to include attributes that describe a plurality of constituent shared content objects stored on one or more storage devices in the cloud-based storage system. An administrator or other user configures allow/deny access privileges to the shareable unit. Upon receiving a request from a user to access the shareable unit, a single access token is generated to provide access to the shared content objects that comprise the shareable unit. Ongoing access to the shareable unit is accomplished using the single access token, without the need to provision an access token or tokens pertaining to individual ones of the constituent shared content objects of the shareable unit.

21 Claims, 10 Drawing Sheets

Related U.S. Application Data

(60) Provisional application No. 62/396,685, filed on Sep. 19, 2016.

(51) Int. Cl.
*G16H 30/20* (2018.01)
*G06F 21/60* (2013.01)

(52) U.S. Cl.
CPC ...... *G06F 21/6218* (2013.01); *G06F 21/6245* (2013.01); *G16H 30/20* (2018.01); *H04L 63/0428* (2013.01); *G06F 2221/2141* (2013.01); *G06F 2221/2145* (2013.01); *H04L 63/0807* (2013.01)

(56) References Cited

U.S. PATENT DOCUMENTS

| | | | |
|---|---|---|---|
| 7,814,436 | B2 | 10/2010 | Schrag |
| 8,296,834 | B2 | 10/2012 | Ritari |
| 8,423,956 | B2 | 4/2013 | Banavar |
| 8,612,298 | B1 | 12/2013 | Talreja |
| 8,817,021 | B1 | 8/2014 | Hickman |
| 8,817,067 | B1 | 8/2014 | Fan |
| 9,015,212 | B2 | 4/2015 | David |
| 9,129,095 | B1 | 9/2015 | Lam |
| 9,183,672 | B1 | 11/2015 | Hickman |
| 9,202,076 | B1 * | 12/2015 | Chazin ............... G06F 21/6218 |
| 9,280,821 | B1 | 3/2016 | Choe |
| 9,288,283 | B2 | 3/2016 | Al ten |
| 9,403,087 | B2 | 8/2016 | Riley |
| 9,645,947 | B2 | 5/2017 | Angelo |
| 9,674,249 | B1 | 6/2017 | Kekre |
| 10,013,157 | B2 | 7/2018 | McKegney et al. |
| 10,032,032 | B2 | 7/2018 | Suarez |
| 10,467,426 | B1 * | 11/2019 | Esposito ............. G06F 16/9024 |
| 10,965,547 | B1 * | 3/2021 | Esposito ................ H04L 67/10 |
| 2003/0090530 | A1 | 5/2003 | Ramani |
| 2004/0034295 | A1 | 2/2004 | Salganicoff |
| 2004/0239679 | A1 | 12/2004 | Ito |
| 2006/0161516 | A1 | 7/2006 | Clarke |
| 2007/0294701 | A1 | 12/2007 | Banavar |
| 2008/0174598 | A1 | 7/2008 | Risenhoover |
| 2008/0246757 | A1 | 10/2008 | Ito |
| 2010/0013842 | A1 | 1/2010 | Green |
| 2010/0045662 | A1 | 2/2010 | Boothroyd |
| 2010/0097375 | A1 | 4/2010 | Tadaishi |
| 2010/0218825 | A1 | 9/2010 | Jee |
| 2012/0159523 | A1 | 6/2012 | Kulkarni |
| 2012/0226663 | A1 | 9/2012 | Valdez Kline |
| 2012/0254881 | A1 | 10/2012 | Hamamoto |
| 2012/0268463 | A1 | 10/2012 | Loberg |
| 2013/0054960 | A1 | 2/2013 | Grab |
| 2013/0120367 | A1 | 5/2013 | Miller |
| 2013/0125029 | A1 | 5/2013 | Miller |
| 2013/0132466 | A1 | 5/2013 | Miller |
| 2013/0219456 | A1 | 8/2013 | Sharma |
| 2013/0222373 | A1 | 8/2013 | Weinstein |
| 2013/0241926 | A1 | 9/2013 | Asaria |
| 2013/0305039 | A1 | 11/2013 | Gauda |
| 2014/0082717 | A1 | 3/2014 | Kang |
| 2014/0165176 | A1 | 6/2014 | Ow |
| 2014/0244700 | A1 | 8/2014 | Aikas |
| 2014/0282921 | A1 | 9/2014 | Filman |
| 2014/0282938 | A1 | 9/2014 | Moisa |
| 2015/0067793 | A1 | 3/2015 | Robison, Jr. |
| 2015/0242466 | A1 | 8/2015 | Alexander |
| 2015/0317571 | A1 | 11/2015 | Maetz |
| 2016/0019278 | A1 | 1/2016 | Jadhav |
| 2016/0134593 | A1 | 5/2016 | Gvili |
| 2016/0217294 | A1 | 7/2016 | Hornquist Astrand |
| 2016/0224677 | A1 | 8/2016 | Goel |
| 2016/0275303 | A1 * | 9/2016 | Narayanaswamy ........................ H04L 63/1458 |
| 2017/0006020 | A1 | 1/2017 | Falodiya |
| 2017/0041254 | A1 | 2/2017 | Agara Venkatesha Rao |
| 2017/0046531 | A1 | 2/2017 | Roberts |
| 2017/0199883 | A1 * | 7/2017 | Terry .................. G06F 21/6218 |
| 2017/0228182 | A1 | 8/2017 | Novak |
| 2017/0235973 | A1 * | 8/2017 | Doshi ................ H04L 67/1002 709/213 |
| 2017/0250940 | A1 | 8/2017 | Chao |
| 2017/0264618 | A1 | 9/2017 | Chandra |
| 2017/0264619 | A1 * | 9/2017 | Narayanaswamy .. H04L 63/105 |
| 2018/0048725 | A1 * | 2/2018 | Doshi .................... H04L 67/22 |
| 2018/0083941 | A1 | 3/2018 | Thakkar |
| 2018/0314847 | A1 * | 11/2018 | Yeo ....................... H04L 9/0631 |
| 2018/0324172 | A1 | 11/2018 | Unnikrishnan |
| 2019/0103968 | A1 | 4/2019 | Srinivasan |
| 2019/0155870 | A1 | 5/2019 | Prakash |
| 2019/0158497 | A1 | 5/2019 | Diaz Cuellar |
| 2019/0179720 | A1 | 6/2019 | Chen |
| 2019/0213649 | A1 * | 7/2019 | Van Biljon ......... G06F 21/6218 |

OTHER PUBLICATIONS

Raghavan, Barath, et al. "Cloud control with distributed rate limiting." ACM SIGCOMM Computer Communication Review 37.4 (2007): 337-348. (Year: 2007).*

"WebGL: Interacting with browser scripting", URL: http://docs.unity3d.com/Manual/webgl-interactingwithbrowserscripting.html, May 2017.

"Interaction Components for your Verold Scenes", URL: https://www.verold.com/blog/posts/interaction-components-for-your-verold-scenes-83, Oct. 2014.

"Browser-Based Integrated Environment", Jun. 2015.

Non-final Office Action dated Dec. 13, 2018 for U.S. Appl. No. 15/455,074.

Notice of Allowance dated Jul. 22, 2019 for U.S. Appl. No. 15/455,074.

Notice of Allowance dated Nov. 1, 2019 for U.S. Appl. No. 15/455,074.

Rajkumar, M. Newlin, V. Venkatesa Kumar, and R. Sivaramakrishnan. "Efficient integrity auditing services for cloud computing using raptor codes." Proceedings of the 2013 Research in Adaptive and Convergent Systems. (pp. 75-78). ACM, 2013. (Year: 2013).

K. Singh and J. Buford, "Developing WebRTC-based team apps with a cross-platform mobile framework," 2016 13th IEEE Annual Consumer Communications & Networking Conference (CCNC), Las Vegas, NV, 2016, pp. 236-242. (Year: 2016).

H. Takabi, J. B. D. Joshi and G. Ahn, "Security and Privacy Challenges in Cloud Computing Environments," in IEEE Security & Privacy, vol. 8, No. 6, pp. 24-31, Nov.-Dec. 2010. (Year: 2010).

S. Ruj, M. Stojmenovic and A. Nayak, "Privacy Preserving Access Control with Authentication for Securing Data in Clouds," 2012 12th IEEE/ACM International Symposium on Cluster, Cloud and Grid Computing (ccgrid 2012), Ottawa, ON, 2012, pp. 556-563. (Year: 2012).

* cited by examiner

SHARING DYNAMICALLY CHANGING UNITS OF CLOUD-BASED CONTENT

RELATED APPLICATIONS

The present application is a continuation application of U.S. patent application Ser. No. 15/455,074 titled "SHARING DYNAMICALLY CHANGING UNITS OF CLOUD-BASED CONTENT", filed Mar. 9, 2017 which claims the benefit of priority to U.S. Provisional Patent Application Ser. No. 62/396,685 titled "SHARING DYNAMICALLY CHANGING UNITS OF CLOUD-BASED CONTENT", filed Sep. 19, 2016, which are all hereby incorporated by reference in their entirety.

BACKGROUND

Electronically stored information objects (e.g., files, images, videos, etc.) are often associated in collections or units so as to perform a certain function. For example, three-dimensional (3D) graphics are rendered using a collection of multiple files, such as model files (e.g., *.obj files), materials files (e.g., *.mtl files), texture files (e.g., *.jpg files), and/or other files. As another example, a website can host viewing or rendering files (e.g., *.html files), style files (e.g., *.css files), script files (e.g., *.js files), image files (e.g., *.jpg or *.png files), and/or other files. As yet another example, a digital imaging and communications in medicine (DICOM) package might comprise hundreds or thousands of image files. The underlying content and dependencies of such amalgamations or units of content can be changed dynamically. Specifically, a texture file referenced by a 3D model file or an MRI scan might be updated, or the model file or DICOM metadata might be modified to reference a new texture file or view. Further, multiple collaborators (e.g., graphics artists, web developers, physicians, etc.) may be associated with the foregoing units of content for development, review, and/or other purposes. In such cases, a cloud-based content management service or platform might be used to facilitate the collaboration.

Unfortunately, legacy techniques for sharing units of cloud-based content present limitations at least as pertaining to efficiently managing access in the presence of dynamically changing aspects of such units. Specifically, some approaches might facilitate secure access to a fixed set of folders comprising a certain set of cloud-based content. However, such approaches restrict the collaborators to working within the boundaries of the shared folders. This can present limitations pertaining to referencing content outside the shared folder boundaries, referencing content within the shared folders by other units of content (e.g., other model files or material files), and/or other activities.

Such limitations introduce severe side-effects such as a need for multiple copies of certain content, or a need for multiple access tokens. Worse, legacy approaches have the potential to permit unauthorized access to content and/or have the potential to severely increase demands on users to manually perform content management operations. The various legacy techniques introduce still other operations and/or factors that reduce the efficiency of sharing or collaboration using a cloud-based service or platform. A technical solution is therefore needed.

What is needed is a technique or techniques to improve over legacy techniques and/or over other considered approaches. Some of the approaches described in this background section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

SUMMARY

The present disclosure provides a detailed description of techniques used in systems, methods, and in computer program products for efficient collaboration over amalgamations of cloud-based shared content in the presence of a dynamically changing amalgamation constituency, which techniques advance the relevant technologies to address technological issues with legacy approaches. More specifically, the present disclosure provides a detailed description of techniques used in systems, methods, and in computer program products for efficient collaboration over amalgamations of cloud-based shared content in the presence of dynamically changing amalgamation constituency. Certain embodiments are directed to technological solutions for implementing a secure manifest file to be used for provisioning access, and for updating the contents of data referenced in the manifest file.

The disclosed embodiments modify and improve over legacy approaches. In particular, the herein-disclosed techniques provide technical solutions that address the technical problems attendant to efficiently and securely sharing collections of cloud-based content having dynamic dependencies and content versions. Such technical solutions relate to improvements in computer functionality. Various applications of the herein-disclosed improvements in computer functionality serve to reduce the demand for computer memory, reduce the demand for computer processing power, reduce network bandwidth use, and reduce the demand for inter-component communication. Some embodiments disclosed herein use techniques to improve the functioning of multiple systems within the disclosed environments, and some embodiments advance peripheral technical fields as well. As one specific example, use of the disclosed techniques and devices within the shown environments as depicted in the figures provide advances in the technical field of collaboration systems as well as advances in various technical fields related to distributed storage systems.

Further details of aspects, objectives, and advantages of the technological embodiments are described herein and in the drawings and claims.

BRIEF DESCRIPTION OF THE DRAWINGS

The drawings described below are for illustration purposes only. The drawings are not intended to limit the scope of the present disclosure.

DETAILED DESCRIPTION

Figure 1:
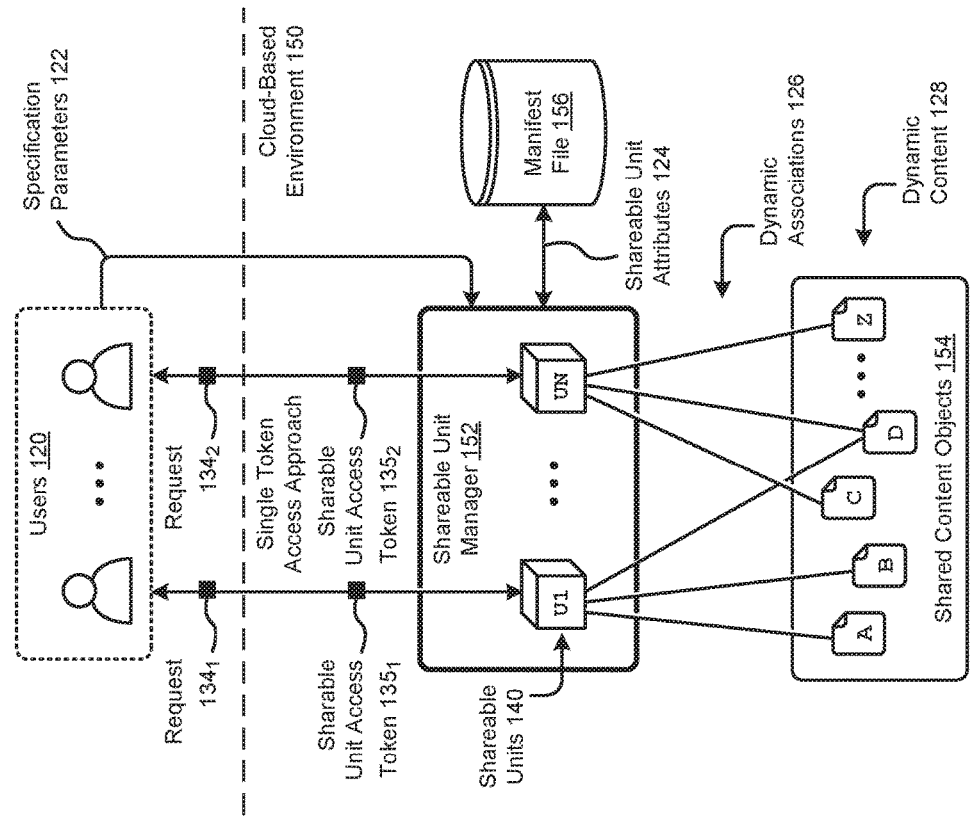
FIG. 1 presents a shareable unit access technique as implemented in systems for efficient collaboration over amalgamations of cloud-based shared content in the presence of dynamically changing amalgamation constituency, according to some embodiments.
Figure 1:
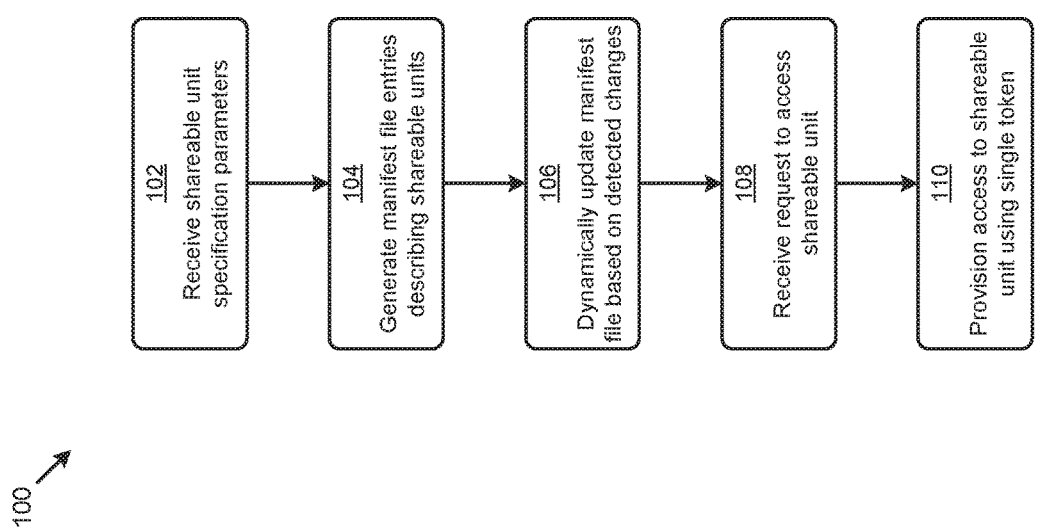

Embodiments in accordance with the present disclosure address the problem of efficiently and securely sharing collections of cloud-based content having dynamically changing dependencies and dynamically changing content versions. Some embodiments are directed to approaches for implementing a secure manifest file to be used for provisioning access to data referenced in the manifest file and for updating the contents the manifest file itself. The accompanying figures and discussions herein present example environments, systems, methods, and computer program products for efficient collaboration over amalgamations of cloud-based shared content in the presence of dynamically changing amalgamation constituency.

Overview

Disclosed herein are techniques for implementing a manifest file accessible by a shareable unit manager to facilitate provisioning access to and updating of dynamic units of cloud-based content. Specifically, in some embodiments, the shareable unit manager generates entries in the manifest file defining various shareable units of cloud-based content. The content, dependencies, versions, collaborators and/or other attributes of the shareable units are specified in the manifest file entries. Access to the shareable units are provisioned to the collaborators using a single access token. In certain embodiments, the shareable unit manager can automatically detect changes (e.g., to content, dependencies, etc.) associated with the shareable units and update the manifest file accordingly. Collaborators can also be provisioned access to a particular version of a shareable unit, or collaborators can be provisioned access to the most recent version of the shareable unit.

Definitions and Use of Figures

Some of the terms used in this description are defined below for easy reference. The presented terms and their respective definitions are not rigidly restricted to these definitions—a term may be further defined by the term's use within this disclosure. The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application and the appended claims, the term "or" is intended to mean an inclusive "or" rather than an exclusive "or". That is, unless specified otherwise, or is clear from the context, "X employs A or B" is intended to mean any of the natural inclusive permutations. That is, if X employs A, X employs B, or X employs both A and B, then "X employs A or B" is satisfied under any of the foregoing instances. As used herein, at least one of A or B means at least one of A, or at least one of B, or at least one of both A and B. In other words, this phrase is disjunctive. The articles "a" and "an" as used in this application and the appended claims should generally be construed to mean "one or more" unless specified otherwise or is clear from the context to be directed to a singular form.

Various embodiments are described herein with reference to the figures. It should be noted that the figures are not necessarily drawn to scale and that elements of similar structures or functions are sometimes represented by like reference characters throughout the figures. It should also be noted that the figures are only intended to facilitate the description of the disclosed embodiments—they are not representative of an exhaustive treatment of all possible embodiments, and they are not intended to impute any limitation as to the scope of the claims. In addition, an illustrated embodiment need not portray all aspects or advantages of usage in any particular environment.

An aspect or an advantage described in conjunction with a particular embodiment is not necessarily limited to that embodiment and can be practiced in any other embodiments even if not so illustrated. References throughout this specification to "some embodiments" or "other embodiments" refer to a particular feature, structure, material or characteristic described in connection with the embodiments as being included in at least one embodiment. Thus, the appearance of the phrases "in some embodiments" or "in other embodiments" in various places throughout this specification are not necessarily referring to the same embodiment or embodiments. The disclosed embodiments are not intended to be limiting of the claims.

Descriptions of Example Embodiments

FIG. 1 presents a shareable unit access technique 100 as implemented in systems for efficient collaboration over amalgamations of cloud-based shared content in the presence of dynamically changing amalgamation constituency. As an option, one or more variations of shareable unit access technique 100 or any aspect thereof may be implemented in the context of the architecture and functionality of the embodiments described herein. The shareable unit access technique 100 or any aspect thereof may be implemented in any environment.

As shown in FIG. 1, a set of users 120 (e.g., collaborators) may want to collaborate over various amalgamations of shared content objects 154 managed by a cloud-based platform in a cloud-based environment 150. According to the herein disclosed techniques, such amalgamations can be presented for access by users 120 as shareable units 140 (e.g., U1, . . . UN) by a shareable unit manager 152. The shareable units 140 can be characterized as having dynamic associations 126 (e.g., changing dependencies, etc.) and dynamic content 128 (e.g., changing content objects, etc.). For example, as can be observed, shared content objects A, B, and D might be associated with shareable unit U1, and shared content objects C, D, and Z might be associated with shareable unit UN. Such associations can change (e.g., be added, be subtracted) over time.

The associations can also result from relationships between the shared content objects. For example, shared content object z might be associated with shareable unit UN due to a dependency of shared content object D on shared content object Z. Further, the shared content objects can change over time. For example, the objects can be updated to create a new version of the object, or can be deleted. The problems attendant to efficiently and securely accessing shareable units 140 having dynamic associations 126 and dynamic content 128 can be addressed by the herein disclosed techniques.

Specifically, shareable unit access technique 100 presents one embodiment of certain operations for efficient collaboration over shareable units of shared content objects 154 in the presence of dynamically changing constituency of the shareable units according to the herein disclosed techniques. Shareable unit access technique 100 can commence with receiving shareable unit specification parameters (operation 102). For example, a set of specification parameters 122 might be received from users 120 at the shareable unit manager 152. The specification parameters are data records to describe certain aspects pertaining to one or more shareable units.

The specification parameters are often organized and/or stored in key-value pairs, where the key is the parameter type and the value is the set of information associated with that parameter. For example, a parameter for identifying a certain shared content object associated with a shareable unit might have a key of "name" and a value of "T2.jpg" (e.g., a texture file named T2.jpg). The shareable unit manager 152 can use the specification parameters 122 and/or other information (e.g., shared content metadata) to generate one or more manifest file entries describing various shareable units (operation 104). For example, shareable unit manager 152 might generate a set of shareable unit attributes 124.

Shareable unit attributes are values or data structures that describe a particular shareable unit. As shown, shareable unit attributes are stored in a manifest file 156. In some variations, the shareable unit attributes are data records to characterize a given shareable unit. The shareable unit attributes are often organized and/or stored in key-value pairs, where the key is the attribute type and the value is the set of information associated with that attribute. For example, an attribute for identifying a parent dependency of a shared content object associated with a shareable unit might have a key of "parent" and a value of "M2" (e.g., a material file named M2.mt1).

According to certain embodiments of the herein disclosed techniques, the shareable unit manager 152 can further dynamically update the manifest file based on detected changes (operation 106). Such updates can use various versioning techniques to facilitate a responsiveness to the presence of a dynamically changing constituency of the shareable units 140. Requests (e.g., request 134₁, request 134₂, etc.) to access any of the shareable units (operation 108) can then be served by efficiently provisioning access to the requested shareable unit using a single token access approach (operation 110). Specifically, in some cases, the shareable units 140 are each treated as a single object with a unique object identifier and accessed using a shareable unit access token (e.g., access token 135₁, access token 135₂, etc.). As used herein, an access token is a code or data structure that is or comprises a value or values that relate a user to one or more operations that are permitted to be performed by the user over one or more storage objects. In exemplary embodiments, such storage objects include shared storage objects. Shared storage objects are any files, folders, directories, directory entries, or metadata pertaining to the foregoing shareable units.

Certain cloud-based storage systems, such as the aforementioned cloud-based storage system, operate in an access regime whereby secure sharing is facilitated by assigning individual ones of the shared storage objects to have individual permissions grantable to a particular two or more users of the cloud-based storage system. Any particular user can have a different set of granted permissions than are granted to other users.

One embodiment of a technique for receiving the shareable unit specification parameters is shown and described as pertaining to FIG. 2.

Figure 2A:
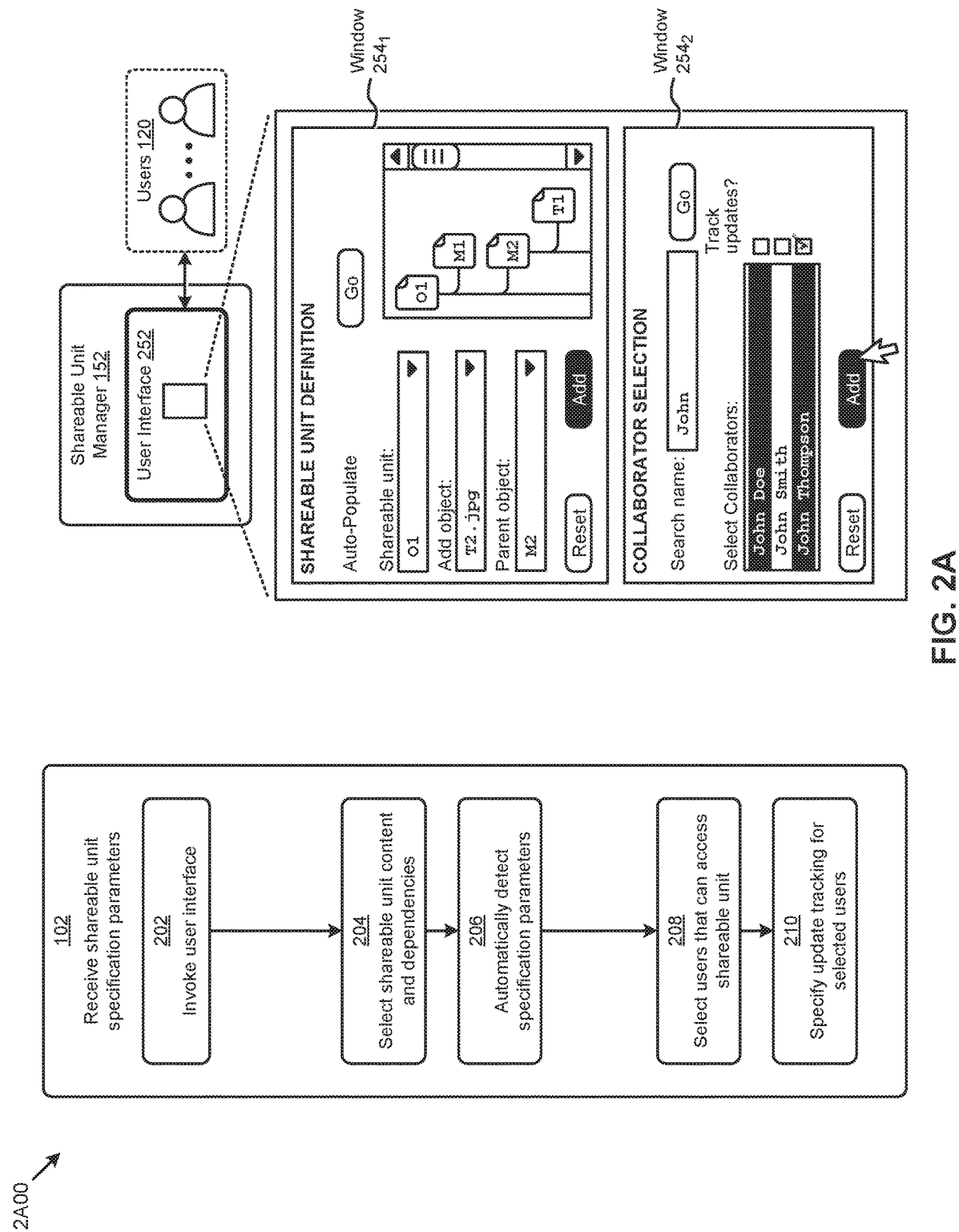
FIG. 2A and FIG. 2B present shareable unit specification techniques to facilitate efficient collaboration over amalgamations of cloud-based shared content in the presence of dynamically changing amalgamation constituency, according to an embodiment.

FIG. 2A presents a shareable unit specification technique 2A00 to facilitate efficient collaboration over amalgamations of cloud-based shared content in the presence of dynamically changing amalgamation constituency. As an option, one or more variations of shareable unit specification technique 2A00 or any aspect thereof may be implemented in the context of the architecture and functionality of the embodiments described herein. The shareable unit specification technique 2A00 or any aspect thereof may be implemented in any environment.

As shown in FIG. 2A, shareable unit specification technique 2A00 presents one embodiment of certain steps for receiving shareable unit specification parameters (operation 102) as implemented by the herein disclosed techniques. Specifically, users 120 can invoke a user interface to facilitate capturing at least some of the specification parameters (step 202). In certain embodiments, a user interface 252 at shareable unit manager 152 comprising various windows (e.g., window 254₁ and window 254₂) can be presented to users 120. Window 254₁ can present various input entry elements (e.g., dropdown selections, text boxes, etc.) through which the users 120 can specify certain parameters, such as content and dependencies, associated with a given shareable unit (step 204). For example, a user can select objects (e.g., T2.jpg) to add to the selected shareable unit (e.g., O1). The parent object (e.g., M2) of the objects comprising the shareable unit can also be specified. A graphical view of the objects and associations (e.g., dependencies) can further be presented in window 254₁. In some embodiments, some or all of the content and/or dependencies and/or other parameters pertaining to a given shareable unit might be automatically detected (step 206). For example, window 254₁ might present a switch to auto-populate such parameters from a preview currently rendered in a certain application.

Window 254₂ can further present various input entry elements (e.g., dropdown selections, text boxes, etc.) through which at least some of the users 120 (e.g., shareable unit owners, system administrators, etc.) can select the users that can have access to certain shareable units (step 208). For example, a user can search for various users and select the users from the search results to add to the access list. In certain embodiments, the user can also select whether allowed accesses (e.g., writes) should be tracked as updates to the shareable unit (step 210). In some cases, access might be constrained to allow access to only a certain version or versions of the shareable unit and/or its constituents.

Figure 2B:
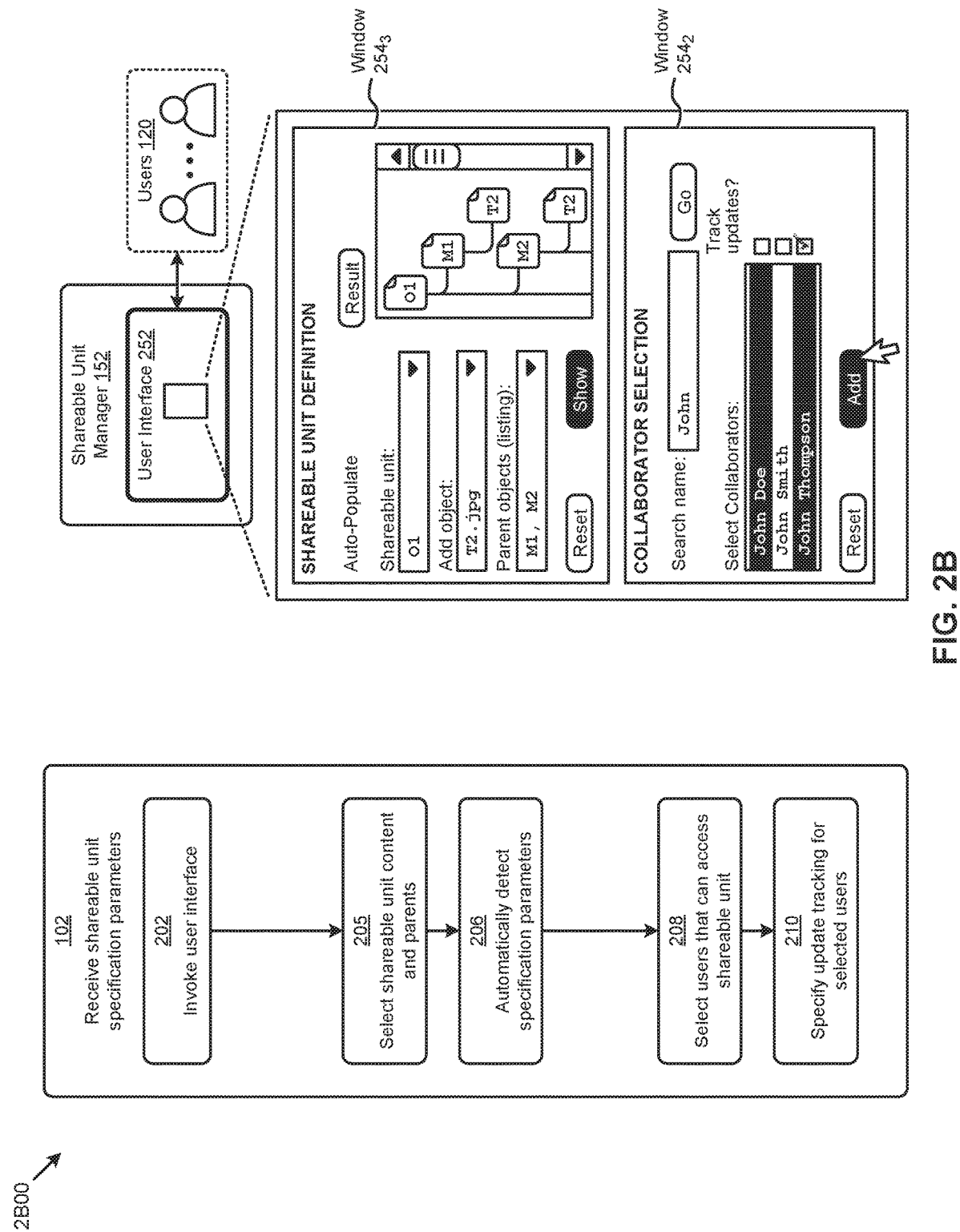

FIG. 2B presents a shareable unit specification technique 2B00 to facilitate efficient collaboration over amalgamations of cloud-based shared content in the presence of dynamically changing amalgamation constituency. As an option, one or more variations of shareable unit specification technique 2B00 or any aspect thereof may be implemented in the context of the architecture and functionality of the embodiments described herein. The shareable unit specification technique 2B00 or any aspect thereof may be implemented in any environment.

As shown in FIG. 2B, shareable unit specification technique 2B00 presents one embodiment of certain steps for receiving shareable unit specification parameters (operation 102) as implemented by the herein disclosed techniques. Specifically, users 120 can invoke a user interface to facilitate capturing at least some of the specification parameters (step 202). In certain situations, a shareable unit specification can include a shareable unit or a shareable unit constituent that is common to two or more parents (e.g., common to two or more objects, or common to two or more levels of hierarchy). Accordingly, in some embodiments, the window $254_3$ includes a series of input entry elements through which the users 120 can specify multiple parents for a particular object (step 205). For example, and as shown, a user can identify a particular object (e.g., T2.jpg) to add to multiple parents of the selected shareable unit (e.g., O1). In this example, the added object T2.jpg has a first parent shown as parent object M1, and also the added object T2.jpg has a second parent shown as parent object M2. A graphical view of the relationships (e.g., hierarchical relationship, object-to-container relationship, etc.) between objects within a relationship hierarchy or relationship mesh is presented as an example, however any other known methods might be used to facilitate assigning an object to multiple parents of a shareable unit. In some cases, one or multiple parent objects can themselves have further ancestors in a hierarchical or non-hierarchical configuration.

The outputs of the shareable unit manager 152 can be stored in a manifest file. One embodiment of a technique for generating manifest file entries from the aforementioned specification parameters and/or other information is shown and described as pertaining to FIG. 3.

Figure 3:
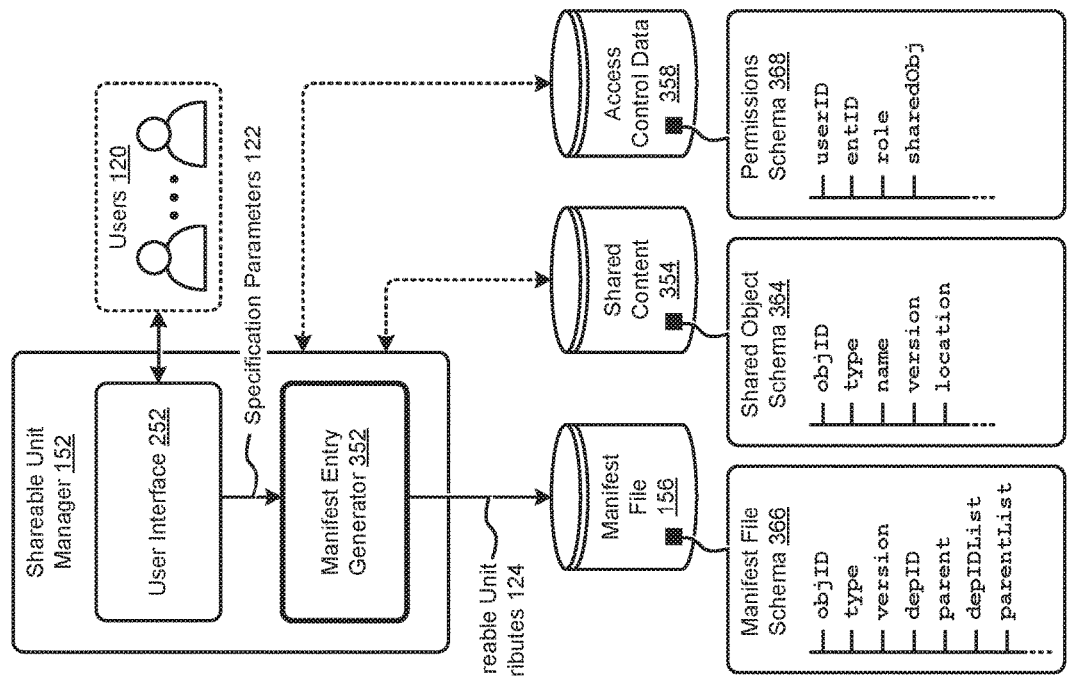
FIG. 3 presents a manifest file entry generation technique for specifying shareable units in systems that provide efficient collaboration over amalgamations of cloud-based shared content in the presence of dynamically changing amalgamation constituency, according to an embodiment.
Figure 3:
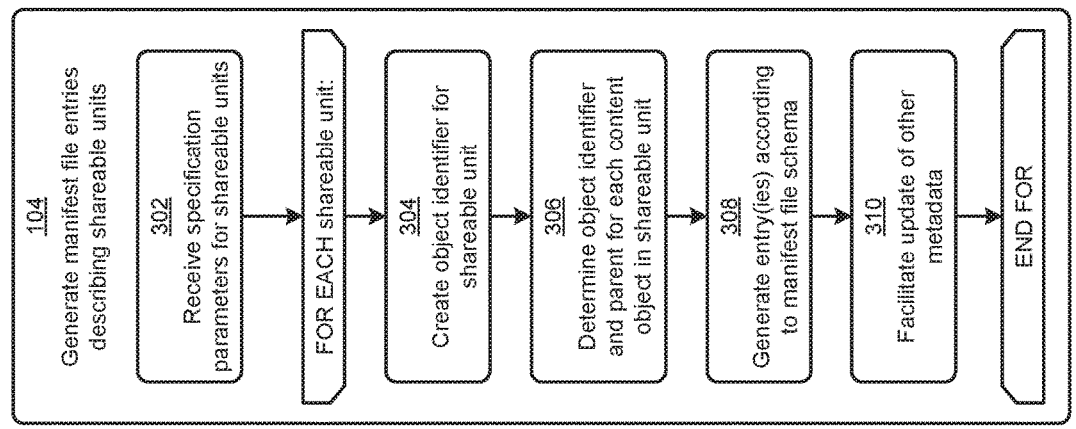

FIG. 3 presents a manifest file entry generation technique 300 for specifying shareable units in systems that provide efficient collaboration over amalgamations of cloud-based shared content in the presence of dynamically changing amalgamation constituency. As an option, one or more variations of manifest file entry generation technique 300 or any aspect thereof may be implemented in the context of the architecture and functionality of the embodiments described herein. The manifest file entry generation technique 300 or any aspect thereof may be implemented in any environment.

The manifest file entry generation technique 300 presented in FIG. 3 is merely one embodiment of certain steps for generating manifest file entries describing shareable units (operation 104) as implemented by the herein disclosed techniques. Specifically, generation of a manifest file entry might be invoked responsive to receiving a set of specification parameters (step 302). In certain embodiments, a manifest entry generator 352 at shareable unit manager 152 can receive such specification parameters (e.g., specification parameters 122) as specified by users 120 at user interface 252.

For each shareable unit processed at the manifest entry generator 352, a unique object identifier for the shareable unit can be generated (step 304). The unique object identifier is a unique sequence of alphanumeric characters used in the cloud-based environment to reference the corresponding shareable unit when performing various operations such as any individual operation or any combinations of indexing operations, searching operations, access control operations, and/or other operations. In some cases, the object identifier can be encrypted.

The manifest entry generator 352 determines the object identifiers and parent dependencies of the shared content objects associated with the shareable unit (step 306). For example, the received specification parameters and metadata describing an available set of shared content 354 can be accessed to determine the shareable unit content characteristics. Specifically, shared content metadata organized according to a shared object schema 364 can be accessed to determine an identifier or objID, a type, a name, a version, a location (e.g., URL), and/or other characteristics of the shareable unit content objects.

Using the foregoing information, one or more entries in the manifest file 156 can be generated according to a manifest file schema 366 (step 308). For example, a set of shareable unit attributes 124 generated by manifest entry generator 352 can be organized in a tabular structure (e.g., relational database table) having rows (e.g., entries) associated with a respective shareable unit and columns associated with certain attributes for each shareable unit. Specifically, according to the example instance of the manifest file schema 366, each entry can indicate the shareable unit object identifier or objID, an object type, a version, a dependent object identifier or depID, a dependent object parent identifier or parent, and/or other attributes. Referring to the heretofore-described mesh and techniques for ascribing multiple parents or ancestors to a particular object, the manifest file schema 366 might include a data structure for a dependent ID or depIDList entry and/or might include a data structure for a parent list or parentList entry.

In some cases, the manifest entry generator 352 can facilitate updates to other metadata associated with the herein disclosed techniques (step 310). For example, the object identifier and/or other attributes of the newly created shareable unit can be added to the metadata describing the shared content 354. Further, access control data 358 can be updated to indicate the users having access to the shareable unit. Such users may be specified in the specification parameters 122 as earlier discussed. As can be observed in the example instance of permissions schema 368 associated with access control data 358, a set of permissions for a given shareable unit might indicate the unique user identifier or userID of the user having access to the shareable unit, an enterprise identifier or entID of the user, a role of the user, the object identifier of the shareable unit or sharedObj, and/or other attributes.

Figure 4A:
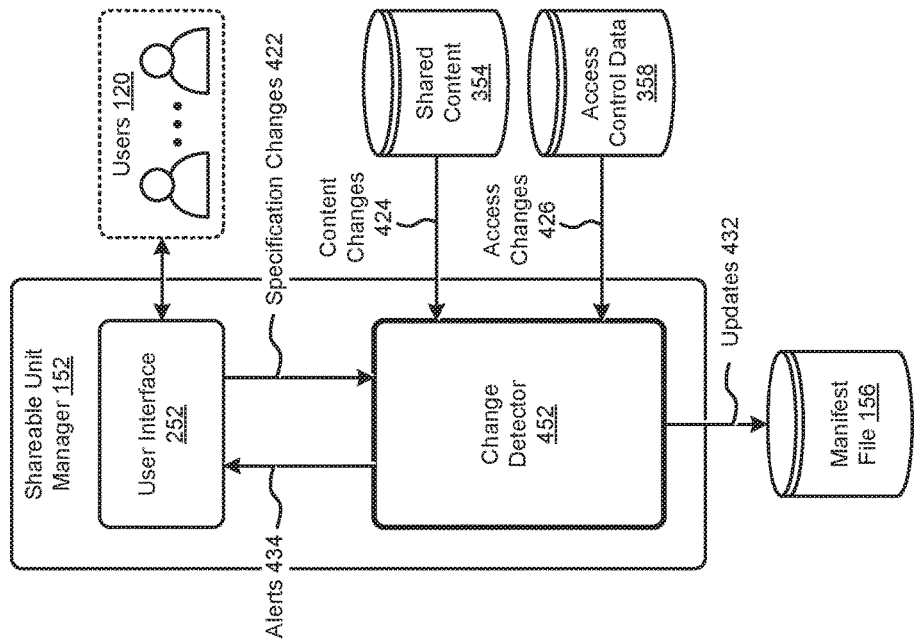
FIG. 4A depicts a dynamic shareable unit update technique for managing shareable units in systems that provide efficient collaboration over amalgamations of cloud-based shared content in the presence of dynamically changing amalgamation constituency, according to an embodiment.
Figure 4A:
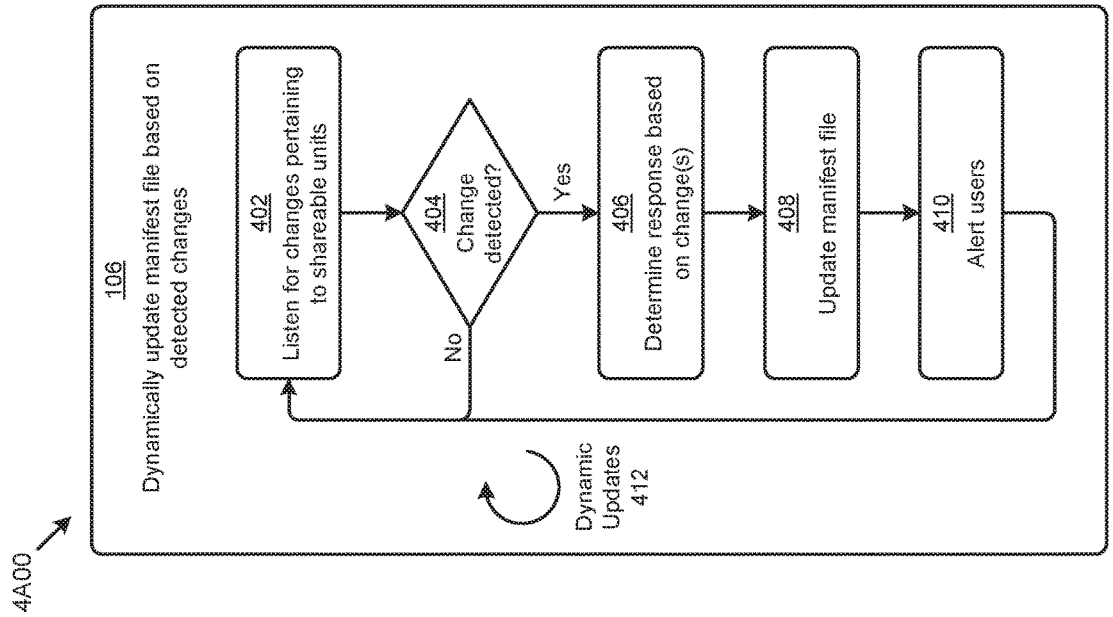

One embodiment of a technique for dynamically updating shareable units is shown and described as pertaining to FIG. 4A.

FIG. 4A depicts a dynamic shareable unit update technique 4A00 for managing shareable units in systems that provide efficient collaboration over amalgamations of cloud-based shared content in the presence of dynamically changing amalgamation constituency. As an option, one or more variations of dynamic shareable unit update technique 4A00 or any aspect thereof may be implemented in the context of the architecture and functionality of the embodiments described herein. The dynamic shareable unit update technique 4A00 or any aspect thereof may be implemented in any environment.

The dynamic shareable unit update technique 4A00 presented in FIG. 4A is one embodiment of certain steps to dynamically update manifest file entries based on detected changes (operation 106) as implemented by the herein disclosed techniques. Specifically, a change detector 452 at the shareable unit manager 152 can listen for changes pertaining to shareable units (step 402). For example, change detector 452 might detect a set of specification changes 422 issued by one or more of the users 120 at user interface 252. Change detector 452 might also detect various instances of content changes 424 pertaining to the shared content 354 associated with shareable units. As another example, access changes 426 as indicated by the access control data 358 might impact one or more shareable units.

If a change corresponding to a shareable unit is detected (see "Yes" path of decision 404), change detector 452 can determine the response or responses to execute as a result of the detected change (step 406). In some cases, a response might comprise one or more updates 432 to the manifest file (step 408). For example, a content change might cause a new version of a shareable unit to be recorded in the manifest file 156. In other cases, a response might comprise one or more alerts 434 sent to user interface 252 for presentation to users 120 (step 410). For example, an alert might be implemented using an email-based alert that is sent to users of the shareable unit that subsumes the content change. In some cases, one content change to a particular object might cause content changes to many other objects in the same shareable unit. In such cases, the many alerts can be amalgamated into a single conglomerate alert. Granularity and filtering of alerts can be selected and/or otherwise managed by a user.

Strictly as further examples, an alert responsive to an access change might display a confirmation request to add a new collaborator on a shareable unit, or display a message indicating a collaborator has been removed by another user. Following such responses, or if no change was earlier detected (see "No" path of decision 404), change detector 452 will continually listen for changes related to shareable units to facilitate the dynamic shareable unit update technique 4A00 (see dynamic updates 412). An example dynamic update scenario is shown and described as pertaining to FIG. 4B.

Figure 4B:
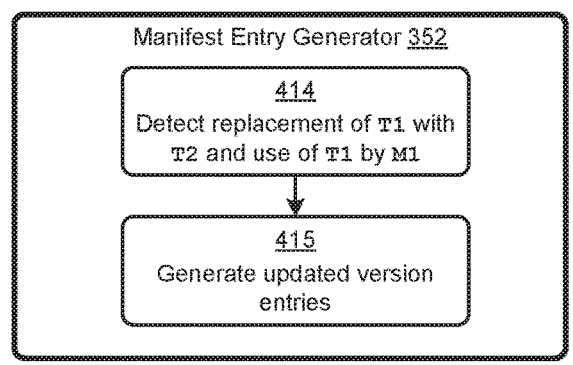
FIG. 4B illustrates a manifest file update scenario as implemented in systems that provide efficient collaboration over amalgamations of cloud-based shared content in the presence of dynamically changing amalgamation constituency, according to an embodiment.

FIG. 4B illustrates a manifest file update scenario 4B00 as implemented in systems that provide efficient collaboration over amalgamations of cloud-based shared content in the presence of dynamically changing amalgamation constituency. As an option, one or more variations of manifest file update scenario 4B00 or any aspect thereof may be implemented in the context of the architecture and functionality of the embodiments described herein. The manifest file update scenario 4B00 or any aspect thereof may be implemented in any environment.

FIG. 4B presents various representative structures illustrating a dynamic manifest file update technique as earlier described. Specifically, a set of manifest file entries $442_1$ can represent a first state of a shareable unit O1. For example, manifest file entries $442_1$ might represent a version O1v33 of a shareable unit comprising a 3D graphics model file O1 with dependencies on material files M1 and M2, a texture file T1, and/or other objects. At some moment in time, the herein disclosed techniques can be implemented to detect a change to the foregoing shareable unit. Specifically, replacement of texture file T1 with texture file T2, and a new association between material file M1 and texture file T1, can be detected (step 414). Such detected changes can invoke an update of the manifest file (step 415). In this example, the change is indicated by manifest file entries $442_2$. As can be observed, manifest file entries $442_2$ preserve the previous version entries 444 (e.g., for version O1v33) for users having access to merely that particular version. Manifest file entries $442_2$ also comprise newly generated entries. Updated version entries 446 correspond to a new version O1v34 of the shareable unit that reflects the detected changes. For example, texture file T2 is shown to be associated with material file M2, and texture file T1 is shown to be associated with material file M1.

The herein disclosed techniques enable the scenario described in FIG. 4B by addressing the problems attendant to efficiently and securely sharing collections of cloud-based content having dynamic dependencies and content versions. One embodiment of a data flow in a system for implementing the herein disclosed techniques is described in FIG. 5.

Figure 5:
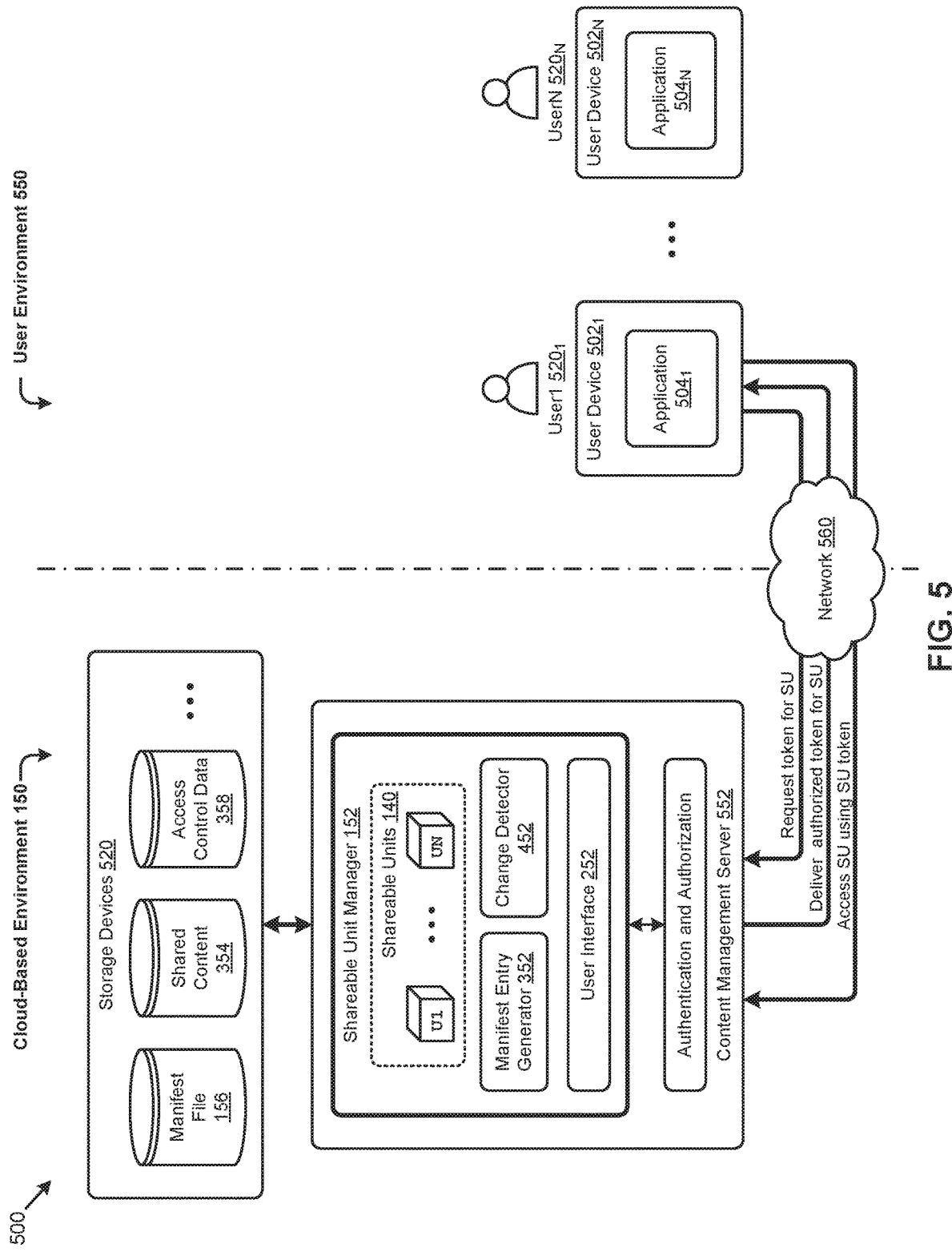
FIG. 5 is a schematic of a data flow to implement techniques for efficient collaboration over amalgamations of cloud-based shared content in the presence of dynamically changing amalgamation constituency, according to an embodiment.

FIG. 5 is a schematic of a data flow 500 to implement techniques for efficient collaboration over amalgamations of cloud-based shared content in the presence of dynamically changing amalgamation constituency. As an option, one or more variations of data flow 500 or any aspect thereof may be implemented in the context of the architecture and functionality of the embodiments described herein. Also, the data flow 500 or any aspect thereof may be implemented in any environment.

The shown data flow depicts multiple representative users (e.g., user1 $520_1$, . . . , userN $520_N$) in a user environment 550 collaborating on various instances of shareable units 140 comprising shared content objects from a cloud-based environment 150. In certain embodiments, such collaboration can be facilitated by an instance of the shareable unit manager 152 operating at a content management server 552 in the cloud-based environment 150. Content management server 552 can facilitate access to storage devices 520 in the cloud-based environment 150 that store various data used by the herein disclosed techniques such as shared content 354, manifest file 156, and access control data 358. As shown, shareable unit manager 152 can further comprise a user interface 252, a manifest entry generator 352, and a change detector 452, as earlier described.

As can be observed, the users can interact with the shareable unit manager 152 at the content management server 552 over a network 560 (e.g., local area network or LAN, wireless LAN or WLAN, wired network, wireless network, the Internet, etc.) using various user devices (e.g., user device $502_1$, . . . , user device $502_N$) such as a desktop computer, a laptop computer, a smart phone, an IP phone, a tablet, and/or another user device. Various applications (e.g., application $504_1$, . . . , application $504_N$) can operate at user devices to, for example, facilitate interaction with the shareable units accessed by the users. For example, the applications might comprise a 3D rendering engine to display a shareable unit corresponding to a 3D model and/or to a set of 3D and/or other graphics rendering parameters. The applications can further facilitate interaction with user interface 252 of the shareable unit manager 152. For example, the application might be a web browser to present the earlier described interaction windows to the users for specification of shareable unit parameters. Other types of applications are possible.

Strictly as an additional application, a set of image files can be stored for multiple user access (e.g., shared) as an amalgamation in an image metadata store, and shared as a single shareable unit. In one example, a DICOM image file might be composed of many image files and/or image file metadata that is used for various purposes. Such a purpose can include viewing in a browser or web application. When a view requested by a user is received by a web application, then constituent images within the shareable unit can be accessed. A display view generator in the web application can then organize (e.g., in a series stack) the associated image files for viewing by the user. Only one access token (i.e., the access token pertaining to the shareable unit) is needed.

The foregoing is merely one example of a digital medical information model that describes an association of digital information files (e.g., comprising image data) that can be used with techniques maintaining logical associations between files when the files are physically stored in dynamically-determined cloud-based storage structures. Specifically, a digital medical information model might correspond to a certain instance of a DICOM file association structure that shows the "Patient" information entity can be the "parent" information entity that has a one to many (e.g., 1:n) relationship with the "Study" information entity. For example, one particular patient might have an association with an MRI scan brain study as well as a CAT scan brain study.

Further, a "Study" can have a one to many relationships with the "Series" information entity. Any of the parent files and/or respective descendant components can be individually collaborated over and individually managed. Changes to the constituents can be detected and modifications made to the manifest file so as to be able to provide secure access to the shareable unit using only a single access token.

Additional Embodiments of the Disclosure

Additional Practical Application Examples

Figure 6:
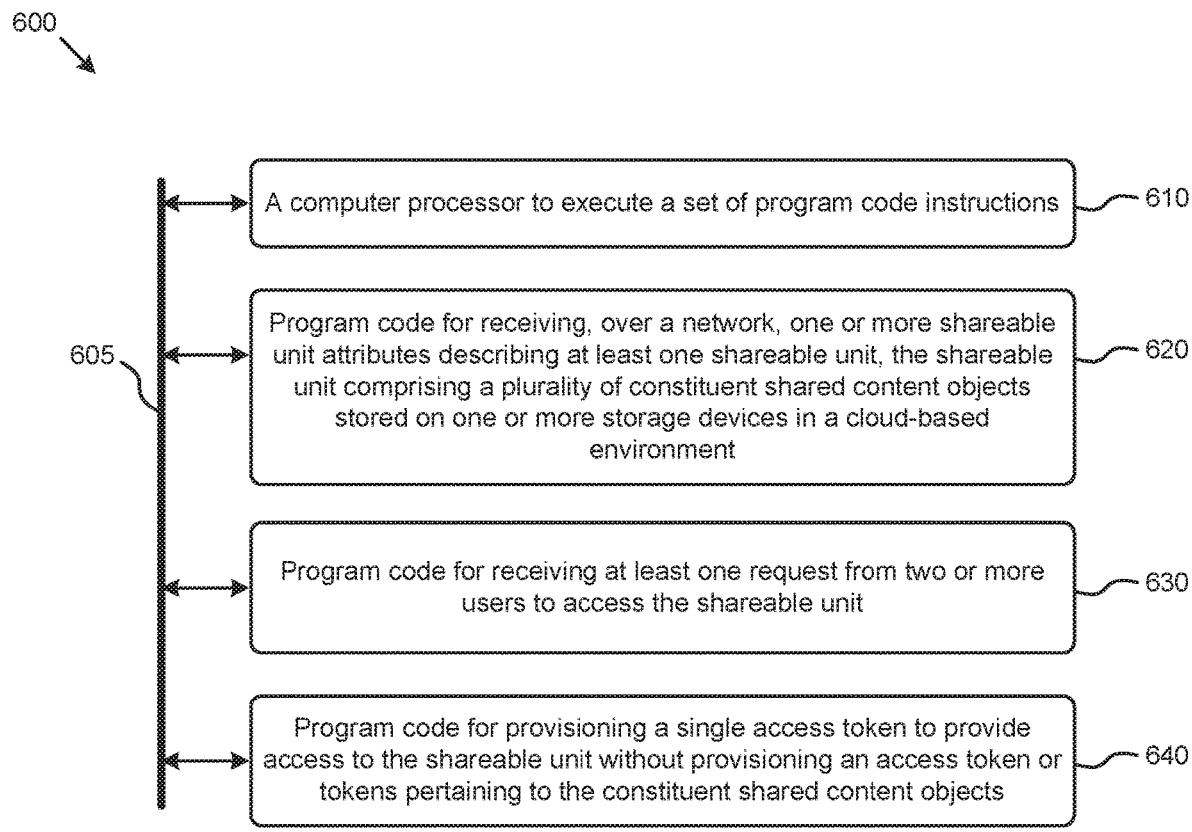
FIG. 6 depicts system components as arrangements of computing modules that are interconnected so as to implement certain of the herein-disclosed embodiments.

FIG. 6 depicts a system 600 as an arrangement of computing modules that are interconnected so as to operate cooperatively to implement certain of the herein-disclosed embodiments. This and other embodiments present particular arrangements of elements that individually, and/or as combined, serve to form improved technological processes that address efficiently and securely sharing collections of cloud-based content having dynamic dependencies and content versions. The partitioning of system 600 is merely illustrative and other partitions are possible. As an option, the system 600 may be implemented in the context of the architecture and functionality of the embodiments described herein. Of course, however, the system 600 or any operation therein may be carried out in any desired environment.

The system 600 comprises at least one processor and at least one memory, the memory serving to store program instructions corresponding to the operations of the system. As shown, an operation can be implemented in whole or in part using program instructions accessible by a module. The modules are connected to a communication path 605, and any operation can communicate with other operations over communication path 605. The modules of the system can, individually or in combination, perform method operations within system 600. Any operations performed within system 600 may be performed in any order unless as may be specified in the claims.

The shown embodiment implements a portion of a computer system, presented as system 600, comprising a computer processor to execute a set of program code instructions (module 610) and modules for accessing memory to hold program code instructions to perform: receiving, over a network, one or more shareable unit attributes describing at least one shareable unit, the shareable unit comprising a plurality of constituent shared content objects stored on one or more storage devices in a cloud-based environment (module 620); receiving at least one request from two or more users to access the shareable unit (module 630); and provisioning a single access token to provide access to the shareable unit without provisioning an access token or tokens pertaining to the constituent shared content objects (module 640).

Variations of the foregoing may include more or fewer of the shown modules. Certain variations may perform more or fewer (or different) steps, and/or certain variations may use data elements in more, or in fewer (or different) operations.

System Architecture Overview

Additional System Architecture Examples

Figure 7A:
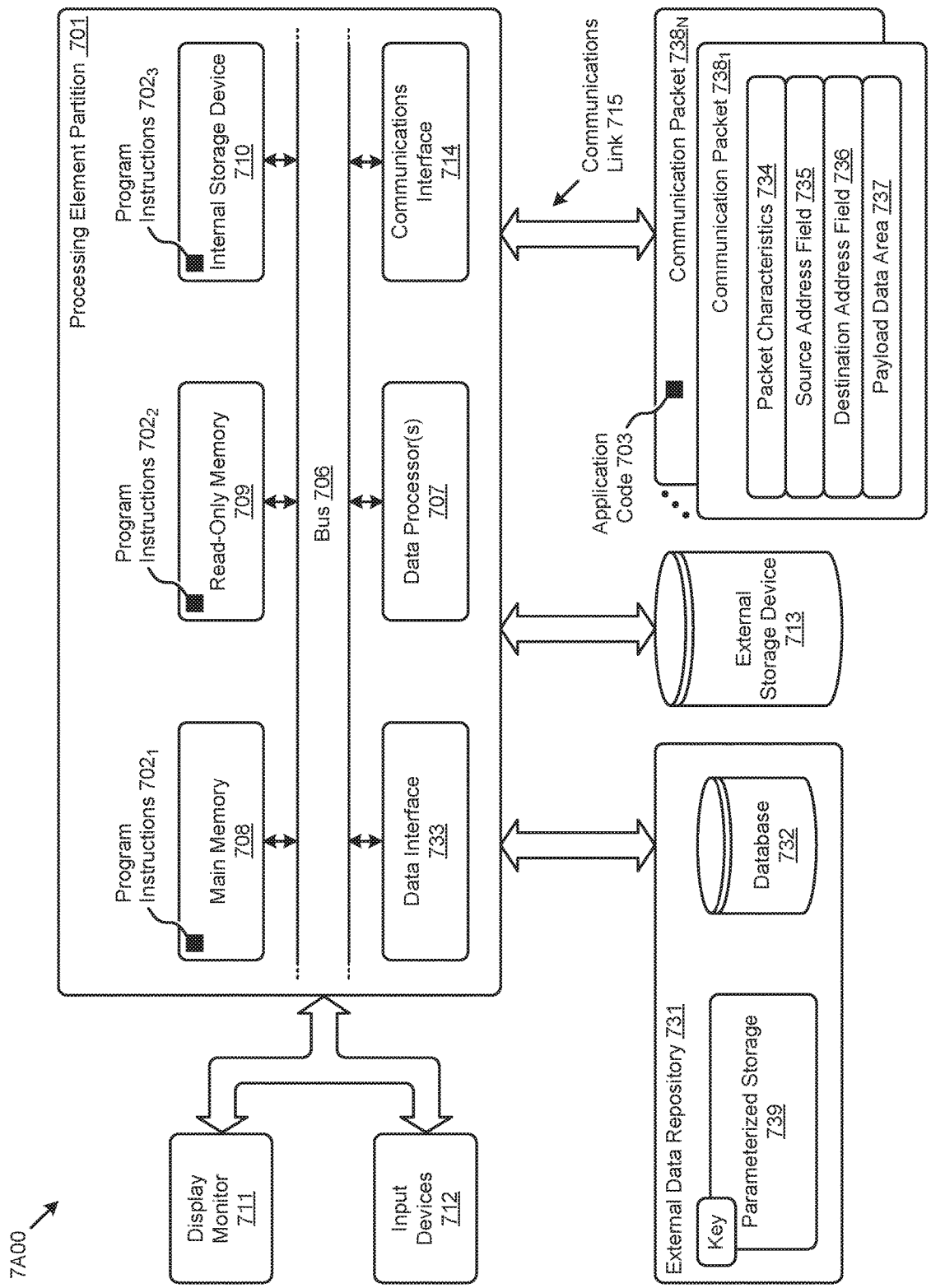
FIG. 7A and FIG. 7B present block diagrams of computer system architectures having components suitable for implementing embodiments of the present disclosure, and/or for use in the herein-described environments.

FIG. 7A depicts a block diagram of an instance of a computer system 7A00 suitable for implementing embodiments of the present disclosure. Computer system 7A00 includes a bus 706 or other communication mechanism for communicating information. The bus interconnects subsystems and devices such as a central processing unit (CPU), or a multi-core CPU (e.g., data processor 707), a system memory (e.g., main memory 708, or an area of random access memory (RAM)), a non-volatile storage device or non-volatile storage area (e.g., read-only memory 709), an internal storage device 710 or external storage device 713 (e.g., magnetic or optical), a data interface 733, a communications interface 714 (e.g., PHY, MAC, Ethernet interface, modem, etc.). The aforementioned components are shown within processing element partition 701, however other partitions are possible. The shown computer system 7A00 further comprises a display 711 (e.g., CRT or LCD), various input devices 712 (e.g., keyboard, cursor control), and an external data repository 731.

According to an embodiment of the disclosure, computer system 7A00 performs specific operations by data processor 707 executing one or more sequences of one or more program code instructions contained in a memory. Such instructions (e.g., program instructions $702_1$, program instructions $702_2$, program instructions $702_3$, etc.) can be contained in or can be read into a storage location or memory from any computer readable/usable storage medium such as a static storage device or a disk drive. The sequences can be organized to be accessed by one or more processing entities configured to execute a single process or configured to execute multiple concurrent processes to perform work. A processing entity can be hardware-based (e.g., involving one or more cores) or software-based, and/or can be formed using a combination of hardware and software that implements logic, and/or can carry out computations and/or processing steps using one or more processes and/or one or more tasks and/or one or more threads or any combination thereof.

According to an embodiment of the disclosure, computer system 7A00 performs specific networking operations using one or more instances of communications interface 714. Instances of the communications interface 714 may comprise one or more networking ports that are configurable (e.g., pertaining to speed, protocol, physical layer characteristics, media access characteristics, etc.) and any particular instance of the communications interface 714 or port thereto can be configured differently from any other particular instance. Portions of a communication protocol can be carried out in whole or in part by any instance of the communications interface 714, and data (e.g., packets, data structures, bit fields, etc.) can be positioned in storage locations within communications interface 714, or within system memory, and such data can be accessed (e.g., using random access addressing, or using direct memory access DMA, etc.) by devices such as data processor 707.

The communications link 715 can be configured to transmit (e.g., send, receive, signal, etc.) any types of communication packets (e.g., communication packet $738_1$, communication packet $738_N$, etc.) comprising any organization of data items. The data items can comprise a payload data area 737, a destination address 736 (e.g., a destination IP address), a source address 735 (e.g., a source IP address), and can include various encodings or formatting of bit fields to populate the shown packet characteristics 734. In some cases the packet characteristics include a version identifier, a packet or payload length, a traffic class, a flow label, etc. In some cases the payload data area 737 comprises a data structure that is encoded and/or formatted to fit into byte or word boundaries of the packet.

In some embodiments, hard-wired circuitry may be used in place of or in combination with software instructions to implement aspects of the disclosure. Thus, embodiments of the disclosure are not limited to any specific combination of hardware circuitry and/or software. In embodiments, the term "logic" shall mean any combination of software or hardware that is used to implement all or part of the disclosure.

The term "computer readable medium" or "computer usable medium" as used herein refers to any medium that participates in providing instructions to data processor 707 for execution. Such a medium may take many forms including, but not limited to, non-volatile media and volatile media. Non-volatile media includes, for example, optical or magnetic disks such as disk drives or tape drives. Volatile media includes dynamic memory such as a random access memory.

Common forms of computer readable media includes, for example, floppy disk, flexible disk, hard disk, magnetic tape, or any other magnetic medium; CD-ROM or any other optical medium; punch cards, paper tape, or any other physical medium with patterns of holes; RAM, PROM, EPROM, FLASH-EPROM, or any other memory chip or cartridge, or any other non-transitory computer readable medium. Such data can be stored, for example, in any form of external data repository 731, which in turn can be formatted into any one or more storage areas, and which can comprise parameterized storage 739 accessible by a key (e.g., filename, table name, block address, offset address, etc.).

Execution of the sequences of instructions to practice certain embodiments of the disclosure are performed by a single instance of the computer system 7A00. According to certain embodiments of the disclosure, two or more instances of computer system 7A00 coupled by a communications link 715 (e.g., LAN, PTSN, or wireless network) may perform the sequence of instructions required to practice embodiments of the disclosure using two or more instances of components of computer system 7A00.

The computer system 7A00 may transmit and receive messages such as data and/or instructions organized into a data structure (e.g., communications packets). The data structure can include program instructions (e.g., application code 703), communicated through communications link 715 and communications interface 714. Received program code may be executed by data processor 707 as it is received and/or stored in the shown storage device or in or upon any other non-volatile storage for later execution. Computer system 7A00 may communicate through a data interface 733 to a database 732 on an external data repository 731. Data items in a database can be accessed using a primary key (e.g., a relational database primary key).

The processing element partition 701 is merely one sample partition. Other partitions can include multiple data processors, and/or multiple communications interfaces, and/or multiple storage devices, etc. within a partition. For example, a partition can bound a multi-core processor (e.g., possibly including embedded or co-located memory), or a partition can bound a computing cluster having plurality of computing elements, any of which computing elements are connected directly or indirectly to a communications link. A first partition can be configured to communicate to a second partition. A particular first partition and particular second partition can be congruent (e.g., in a processing element array) or can be different (e.g., comprising disjoint sets of components).

A module as used herein can be implemented using any mix of any portions of the system memory and any extent of hard-wired circuitry including hard-wired circuitry embodied as a data processor 707. Some embodiments include one or more special-purpose hardware components (e.g., power control, logic, sensors, transducers, etc.). Some embodiments of a module include instructions that are stored in a memory for execution so as to implement algorithms that facilitate operational and/or performance characteristics pertaining to efficient collaboration over amalgamations of cloud-based shared content in the presence of dynamically changing amalgamation constituency. A module may include one or more state machines and/or combinational logic used to implement or facilitate the operational and/or performance characteristics pertaining to using amalgamations of cloud-based shared content in the presence of dynamically changing amalgamation constituency.

Various implementations of the database 732 comprise storage media organized to hold a series of records or files such that individual records or files are accessed using a name or key (e.g., a primary key or a combination of keys and/or query clauses). Such files or records can be organized into one or more data structures (e.g., data structures used to implement or facilitate aspects of efficient collaboration over amalgamations of cloud-based shared content in the presence of dynamically changing amalgamation constituency). Such files, records, or data structures can be brought into and/or stored in volatile or non-volatile memory. More specifically, the occurrence and organization of the foregoing files, records, and data structures improve the way that the computer stores and retrieves data in memory, for example, to improve the way data is accessed when the computer is performing operations pertaining to efficient collaboration over amalgamations of cloud-based shared content in the presence of dynamically changing amalgamation constituency, and/or for improving the way data is manipulated when performing computerized operations pertaining to implementing a secure manifest file to be used for provisioning access to and for updating of contents referenced in the manifest file.

Figure 7B:
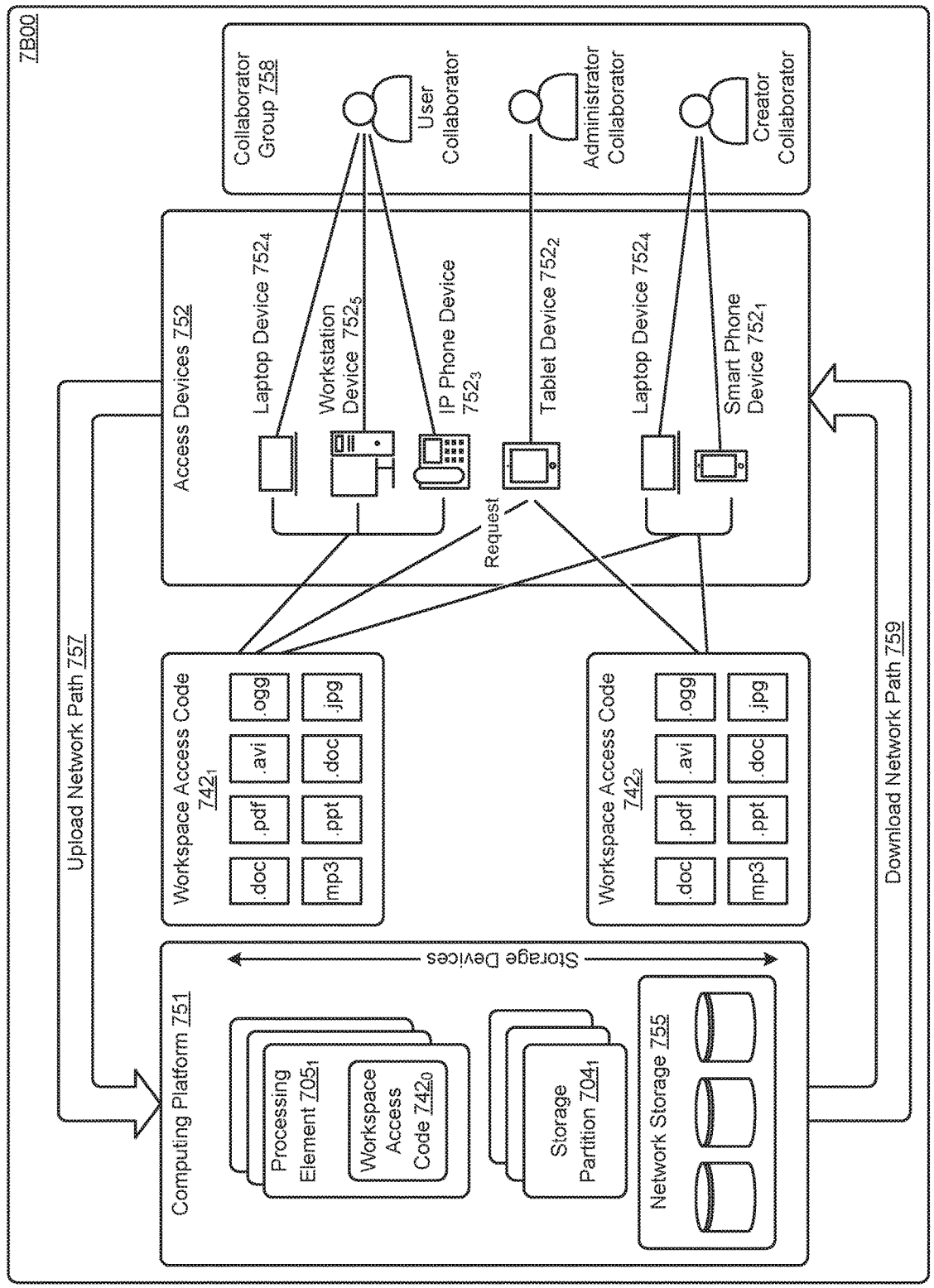

FIG. 7B depicts a block diagram of an instance of a cloud-based collaboration environment 7B00. Such a cloud-based collaboration environment supports access to workspaces through the execution of workspace access code (e.g., workspace access code 742$_0$, workspace access code 742$_1$, and workspace access code 742$_2$). Workspace access code can be executed on any of the shown access devices 752 (e.g., laptop device 752$_4$, workstation device 752$_5$, IP phone device 752$_3$, tablet device 752$_2$, smart phone device 752$_1$, etc.). A group of users can form a collaborator group 758, and a collaborator group can be composed of any types or roles of users. For example, and as shown, a collaborator group can comprise a user collaborator, an administrator collaborator, a creator collaborator, etc. Any user can use any one or more of the access devices, and such access devices can be operated concurrently to provide multiple concurrent sessions and/or other techniques to access workspaces through the workspace access code.

A portion of workspace access code can reside in and be executed on any access device. Any portion of the workspace access code can reside in and be executed on any computing platform 751, including in a middleware setting.

As shown, a portion of the workspace access code resides in and can be executed on one or more processing elements (e.g., processing element $705_1$). The workspace access code can interface with storage devices such as the shown networked storage 755. Storage of workspaces and/or any constituent files or objects, and/or any other code or scripts or data can be stored in any one or more storage partitions (e.g., storage partition $704_1$). In some environments, a processing element includes forms of storage, such as RAM and/or ROM and/or FLASH, and/or other forms of volatile and non-volatile storage.

A stored workspace can be populated via an upload (e.g., an upload from an access device to a processing element over an upload network path 757). A stored workspace can be delivered to a particular user and/or shared with other particular users via a download (e.g., a download from a processing element to an access device over a download network path 759).

In the foregoing specification, the disclosure has been described with reference to specific embodiments thereof. It will however be evident that various modifications and changes may be made thereto without departing from the broader spirit and scope of the disclosure. For example, the above-described process flows are described with reference to a particular ordering of process actions. However, the ordering of many of the described process actions may be changed without affecting the scope or operation of the disclosure. The specification and drawings are to be regarded in an illustrative sense rather than in a restrictive sense.

What is claimed is:

1. A method comprising:
   assigning individual ones of the shared content objects to have individual permissions grantable to one or more users of a cloud-based storage system;
   receiving one or more shareable unit attributes describing a shareable unit, the shareable unit comprising one or more constituent content objects stored on one or more storage devices in the cloud-based storage system, the one or more constituent content objects corresponding to constituent images organized in a particular order for viewing the shareable unit by the one or more users;
   receiving a request from a user of the one or more users to access the shareable unit; and
   provisioning a single access token to provide access to the shareable unit without provisioning an access token or tokens pertaining to individual ones of the one or more constituent content objects of the shareable unit, wherein the single access token covers access to both the shareable unit and constituents of the shareable unit.

2. The method of claim 1, further comprising automatically generating at least a portion of the shareable unit attributes.

3. The method of claim 2, wherein automatically generating the portion of the shareable unit attributes is based at least in part on at least one of one or more user specifications, a hierarchical relationship, or a set of rendering parameters.

4. The method of claim 1, further comprising:
   detecting a change to a constituent of the shareable unit; and
   updating at least one of the shareable unit attributes based at least in part on the change.

5. The method of claim 4, wherein the detecting comprises identifying a change, the change being at least one of a write operation, an access control operation, a dependency change operation, or a content change that pertains to at least one of the shared content objects.

6. The method of claim 5 further comprising:
   accessing a manifest file pertaining to at least one of the shared content objects; and
   updating the manifest file to indicate the change.

7. The method of claim 4, wherein the shareable unit attributes describe at least one of a version identifier of the shareable unit, or version identifiers of constituents of the shareable unit.

8. The method of claim 7, wherein provisioning a single access token is based at least in part on the version identifier of the shareable unit.

9. A computer readable medium, embodied in a non-transitory computer readable medium, the non-transitory computer readable medium having stored thereon a sequence of instructions which, when stored in memory and executed by one or more processors causes the one or more processors to perform a set of acts, the set of acts comprising:
   assigning individual ones of the shared content objects to have individual permissions grantable to one or more users of a cloud-based storage system;
   receiving one or more shareable unit attributes describing a shareable unit, the shareable unit comprising one or more constituent content objects stored on one or more storage devices in the cloud-based storage system, the one or more constituent content objects corresponding to constituent images organized in a particular order for viewing the shareable unit by the one or more users;
   receiving a request from a user of the one or more users to access the shareable unit; and
   provisioning a single access token to provide access to the shareable unit without provisioning an access token or tokens pertaining to individual ones of the one or more constituent content objects of the shareable unit, wherein the single access token covers access to both the shareable unit and constituents of the shareable unit.

10. The computer readable medium of claim 9, further comprising instructions which, when stored in memory and executed by the one or more processors causes the one or more processors to perform acts of automatically generating at least a portion of the shareable unit attributes.

11. The computer readable medium of claim 10, wherein automatically generating the portion of the shareable unit attributes is based at least in part on at least one of one or more user specifications, a hierarchical relationship, or a set of rendering parameters.

12. The computer readable medium of claim 9, further comprising instructions which, when stored in memory and executed by the one or more processors causes the one or more processors to perform acts of:
    detecting a change to a constituent of the shareable unit; and
    updating at least one of the shareable unit attributes based at least in part on the change.

13. The computer readable medium of claim 12, wherein the detecting comprises identifying a change, the change being at least one of a write operation, an access control operation, a dependency change operation, or a content change that pertains to at least one of the shared content objects.

14. The computer readable medium of claim 13 further comprising instructions which, when stored in memory and executed by the one or more processors causes the one or more processors to perform acts of:

accessing a manifest file pertaining to at least one of the shared content objects; and updating the manifest file to indicate the change.

15. The computer readable medium of claim 12, wherein the shareable unit attributes describe at least one of a version identifier of the shareable unit, or version identifiers of constituents of the shareable unit.

16. The computer readable medium of claim 15, wherein provisioning a single access token is based at least in part on the version identifier of the shareable unit.

17. A system comprising:
a storage medium having stored thereon a sequence of instructions; and
one or more hardware processors that execute the instructions to cause the one or more processors to perform a set of acts, the acts comprising,
assigning individual ones of the shared content objects to have individual permissions grantable to one or more users of a cloud-based storage system;
receiving one or more shareable unit attributes describing a shareable unit, the shareable unit comprising one or more constituent content objects stored on one or more storage devices in the cloud-based storage system, the one or more constituent content objects corresponding to constituent images organized in a particular order for viewing the shareable unit by the one or more users;
receiving a request from a user of the one or more users to access the shareable unit; and
provisioning a single access token to provide access to the shareable unit without provisioning an access token or tokens pertaining to individual ones of the one or more constituent content objects of the shareable unit, wherein the single access token covers access to both the shareable unit and constituents of the shareable unit.

18. The system of claim 17, further comprising instructions which, when stored in the storage medium and executed by the one or more hardware processors cause the one or more hardware processors to perform acts of automatically generating at least a portion of the shareable unit attributes.

19. The system of claim 18, wherein automatically generating the portion of the shareable unit attributes is based at least in part on at least one of one or more user specifications, a hierarchical relationship, or a set of rendering parameters.

20. The system of claim 17, further comprising instructions which, when stored in the storage medium and executed by the one or more hardware processors cause the one or more hardware processors to perform acts of:
detecting a change to a constituent of the shareable unit; and
updating at least one of the shareable unit attributes based at least in part on the change.

21. The system of claim 20, wherein the detecting comprises identifying a change, the change being at least one of a write operation, an access control operation, a dependency change operation, or a content change that pertains to at least one of the shared content objects.

* * * * *